(12) United States Patent
Kleinberg

(10) Patent No.: US 6,346,813 B1
(45) Date of Patent: *Feb. 12, 2002

(54) MAGNETIC RESONANCE METHOD FOR CHARACTERIZING FLUID SAMPLES WITHDRAWN FROM SUBSURFACE FORMATIONS

(75) Inventor: Robert L. Kleinberg, Ridgefield, CT (US)

(73) Assignee: Schlumberger Technology Corporation, Ridgefield, CT (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/133,234

(22) Filed: Aug. 13, 1998

(51) Int. Cl.⁷ .................................................. G01U 3/00
(52) U.S. Cl. ...................................................... 324/303
(58) Field of Search ................................ 324/303, 300, 324/338, 339, 314

(56) References Cited

U.S. PATENT DOCUMENTS

| | | | | |
|---|---|---|---|---|
| 2,912,641 | A | | 11/1959 | Ruble .............................. 324/5 |
| 3,597,681 | A | * | 8/1971 | Huckabay et al. ........... 324/303 |
| 4,291,271 | A | | 9/1981 | Lauffer ........................ 324/307 |
| 4,629,986 | A | * | 12/1986 | Clow et al. .................. 324/303 |
| 4,860,581 | A | | 8/1989 | Zimmerman et al. .......... 73/155 |
| 4,994,777 | A | | 2/1991 | Leupold et al. .............. 335/302 |
| 5,023,551 | A | | 6/1991 | Kleinberg et al. ........... 324/303 |
| 5,055,787 | A | * | 10/1991 | Kleinberg et al. ........... 324/303 |
| 5,306,640 | A | | 4/1994 | Vinegar et al. ................ 436/29 |
| 5,428,291 | A | * | 6/1995 | Thomann et al. ............ 324/303 |
| 5,705,927 | A | * | 1/1998 | Sezginer et al. ............. 324/303 |
| 6,111,408 | A | * | 8/2000 | Blades et al. ................ 324/303 |

FOREIGN PATENT DOCUMENTS

| | | | |
|---|---|---|---|
| GB | 2 291 198 A | 1/1996 | ............. G01F/1/56 |
| WO | WO98/59220 | 12/1998 | |

OTHER PUBLICATIONS

Amyx, James W. et al., *Multicomponent Systems, Petroleum Reservoir Engineering* (1960) p. 458.
Andrew, *Nuclear Magnetic Resonance* (1955), p. 127.
Bloembergen, N. et al., *Relaxation Effects in Nuclear Magnetic Resonance Absorption, Physical Review*, 73 (1948) pp. 679–712.
Botto, Robert E., Fossil Fuels, *Encyclopedia of Nuclear Magnetic Resonance* (1996).
Bradley, H,B., ed., Society of Petroleum Engineers, *Petroleum Engineering Handbook* (1992) Chapter 24.
Caprihan, A. and Fukushima, E., *Flow Measurements by NMR, Physics Reports*, 198 (1990) pp. 195–235.
CMR* *Combinable Magnetic Resonance Tool Client Operating Guide*, Schlumberger CMR Operating Guide, First Edition, Jun. 1996.
CRC Handbook of Chemistry and Physics, *CRC Press*, p. B–73 et seq.

(List continued on next page.)

Primary Examiner—Hezron Williams
Assistant Examiner—Dixomara Vargas
(74) Attorney, Agent, or Firm—Eric W. Kuo; William B. Batzer; Mark Levy

(57) ABSTRACT

Magnetic resonance techniques, e.g., nuclear magnetic resonance (NMR) and electron spin resonance (ESR), are used in a fluid sampling tool that extracts a fluid from subsurface earth formations into a flow channel within the tool. The magnetic resonance techniques involve applying a static magnetic field and an oscillating magnetic field to the fluid in the flow channel, and magnetic resonance signals are detected from the fluid and analyzed to extract information about the fluid such as composition, viscosity, etc.

53 Claims, 6 Drawing Sheets

OTHER PUBLICATIONS

Dechter, *Progress in Inorganic Chemistry*, 29 (1982) pp. 285–385.

Dyer, John R., *Applications of Absorption Spectroscopy of Organic Compounds, Prentice–Hall* (1965), pp. 84–85.

Halbach, K., Design of Permanent Multipole Magnets with Oriented Rare Earth Cobalt Material, *Nuc. Inst. Methods* 169, (1980) pp. 1–10.

Halbach, K., Physical and Optical Properties of Rare Earth Cobalt Magnets, *Nuc. Inst. Methods* 187, (1981) pp. 109–117.

Horkowitz, John P. et al., Residual Oil Saturation Measurements in Carbonates with Pulsed NMR Logs, SPWLA 36$^{th}$ Annual Logging Symposium, (Jun 26–29, 1995), Paper Q.

Kleinberg, R. L. and Flaum, C. Review: NMR Detection and Characterization of Hydrocarbons in Subsurface Earth Formations in *Spatially Resolved Magnetic Resonance: Methods and Applications in Materials Science*, Agriculture and Biomedicine, B. Blumich, et al. eds. (1998).

Kleinberg, R.L. and Vinegar, H. J., NMR Properties of Reservoir Fluids, *Log Analyst* (Nov.–Dec. 1996) pp. 20–32.

Kleinberg, R.L., Well Logging, *Encyclopedia of Nuclear Magnetic Resonance,* John Wiley & Sons (1996) vol. 8, pp. 4960–4969.

Li, J.C.M., Chang, P. Self Diffusion Coefficient and Viscosity in Liquids, *Journal Chem. Phys.,* (1955) pp. 518–520.

Low, William, Paramagnetic Resonance in Solids,*Academic Press*, NY (1960) pp. 180–193.

Morriss, C.E. et al., Hydrocarbon Saturation and Viscosity Estimation from NMR Logging in the Belridge Diatomite, *Log Analyst* (Mar.–Apr. 1997) pp. 44–59.

Petrakis and Edelheit, *Applied Spectroscopy Reviews* 15 (1979), p. 195.

Rummens, Frans H.A. and Mourits, Frank M., Intermolecular Interactions in Nuclear Magnetic Resonance.XI. The $^{13}$C and Proton Medium Shifts of $CH_4$ in the Gas Phase and in Solution, *Canadian Journal of Chemistry,* 55 (1977) p. 3021.

Schlumberger's Versatile, Effecient MDT Tool Makes the Complexities of Reservoir Dynamics Understandable, Schlumberger Brochure.

Singer, J.M., Johnston, L. Kleinberg, R.L., and Flaum, C., Fast NMR Logging for bound Fluid and Permeability, SPWLA 38$^{th}$ Annual Logging Symposium (1997) Paper YY, Section 3.

Straley, Christian, An Experimental Investigation of Methane in Rock Materials, SPWLA 38$^{th}$ Annual Logging Symposium (1997) Paper AA.

Tissot, B.P. and Welte, D.H., Petroleum Formation and Occurrence, *Springer–Verlag* (1978) Fig IV.1.20.

Turner, R. Gradient Coil Systems, *Encyclopedia of Nuclear Magnetic Resonance* (1996).

Vinegar, H.J. et al., Whole Core Analysis by $^{13}$C NMR, *SPE Formation Evaluation* 6 (Jun. 1991) pp. 183–189.

Zimmerman, T., et al., Application of Emerging Wireline Formation Testing Technologies,*Eighth Offshore South East Asia Conf.* (OSEA 90105), (Dec. 4–7, 1990).

\* cited by examiner

MAGNETIC RESONANCE METHOD FOR CHARACTERIZING FLUID SAMPLES WITHDRAWN FROM SUBSURFACE FORMATIONS

BACKGROUND OF THE INVENTION

1. Field of the Invention

The present invention relates to well logging tools and methods, and more particularly to methods for analyzing extracted formation fluids by magnetic resonance techniques, especially nuclear magnetic resonance (NMR) and electron spin resonance (ESR).

2. Background Information

Downhole formation fluid sampling tools, such as the Schlumberger Modular Formation Dynamics Tester (MDT), withdraw samples of fluids from earth formations for subsequent analyses. These analyses are needed to characterize physical properties such as water and oil volume fractions, oil viscosity, and water salinity, among others. This knowledge is needed to interpret wireline well logs, and to plan for the efficient exploitation of the reservoir.

In an undisturbed reservoir, formation fluids sometimes partially support the overburden pressure of the earth. When a fluid-bearing formation is penetrated by drilling, formation fluids will flow into the borehole if it is at a lower pressure. The uncontrolled escape of combustible hydrocarbons to the surface ("blowout"), is extremely dangerous, so oil wells are drilled under pressure. During drilling, fluid ("mud") is circulated through the well to carry rock chips to the surface. The mud is densified with heavy minerals such as barite (barium sulfate, 4.5 g/cm$^3$) to ensure that borehole pressure is higher than formation pressure. Consequently, fluid is forced into the formation from the borehole ("invasion"). Usually particles are prevented from entering the formation by the filtering action of the porous rock. Indeed, the filtration process is self-limiting because solids, purposely mixed in the drilling fluid, form a filter cake ("mud cake") at the surface of the borehole. Nonetheless liquid ("mud filtrate") can penetrate quite deeply—as much as several meters into the formation. The filtrate can be either water with various soluble ions, or oil, depending on the type of mud used by the driller. Therefore, the fluid samples withdrawn are mixtures of native formation fluids (including gas, oil and/or water) and the filtrate of mud that was used to drill the well.

Sample contamination of formation fluids by mud filtrate is universally regarded as the most serious problem associated with downhole fluid sampling. It is essential that formation fluid, not mud filtrate, is collected in the sample chambers of the tool. Therefore fluid from the formation is pumped through the tool and into the borehole until it is believed contamination has been reduced to an acceptable level. Thus it is necessary to detect mud filtrate in the fluid sample, to decide when to stop pumping the fluid through the tool and to start collecting it for analysis.

Several measurements are routinely made in fluid sampling tools to detect mud filtrate contamination:

Resistivity indicates the presence of water. The measurement uses the low frequency electrode technique. Unless there is a continuous conducting path between the electrodes, there is no sensitivity to the presence of water. Even with a conducting path, the method is unable to separate the effects of water volume, salinity, and flow geometry. The measurement is simple and often useful, but inherently nonquantitative.

Dielectric constant can distinguish oil from water, but not one oil from another. Moreover the dielectric constant measurement depends on the flow regime of oil/water mixtures.

Flow line pressure and temperature provide no information on fluid properties.

Optical Fluid Analyzers (e.g. Schlumberger OFA) can detect contamination in many cases. It is particularly effective when the mud filtrate is aqueous and the flowing formation fluid is pure hydrocarbon, since there is a large contrast between water and oil in the near infrared band. However, it does less well when the filtrate is oil based, or when the formation fluid is a mixture of oil and water.

Thus, no presently deployed system is generally useful for determining the contamination level of sampled formation fluids. There is a clear need for an apparatus and method which monitors contamination while the sample is being taken, and indicates when contamination has been reduced to an acceptably low level.

Downhole formation fluid sampling tools can withdraw samples of fluids from earth formations and transport them to the surface. The samples are sent to fluid analysis laboratories for analysis of composition and physical properties. There are many inefficiencies inherent in this process.

Only about six samples can be collected on each descent ("trip") of the tool into the borehole. Because fluid sampling tools are deployed from drilling rigs, and because the rental charge for such rigs can exceed $150,000 per day in the areas where fluid sampling is most often conducted, economic considerations usually preclude multiple trips in the hole. Thus, oil producing formations are almost always undersampled.

The samples undergo reversible and irreversible changes as a result of the temperature and/or pressure changes while being brought to the surface, and as a result of the transportation process. For example, gases come out of solution, waxes precipitate, and asphaltenes chemically recombine. Irreversible changes eliminate the possibility of ever determining actual in situ fluid properties. Reversible changes are deleterious because they occur slowly and therefore impact sample handling and measurement efficiency.

The transportation and handling of fluids uphole entails all the dangers associated with the handling of volatile and flammable fluids at high pressure and temperature. After analyses are complete, the samples must be disposed of in an environmentally acceptable manner, with associated financial and regulatory burdens.

Because fluid analysis laboratories are frequently distant from the well site, there is substantial delays—often several weeks—in obtaining results. If a sample is for some reason corrupted or lost during sampling, transportation, or measurement, there is no possibility of returning to the well to replace it.

Thus there is a clear need for immediate analysis of fluid samples at formation temperature and pressure within the downhole sampling tool.

SUMMARY OF THE INVENTION

Magnetic resonance, e.g., nuclear magnetic resonance (NMR) and electronic spin resonance (ESR) can be used to monitor contamination and analyze fluid samples in fluid sampling tools as fluid draw-down proceeds. Measurements are performed in the flow line itself. The methods are inherently noninvasive and noncontacting. Since magnetic resonance measurements are volumetric averages, they are insensitive to flow regime, bubble size, and identity of the continous phase. Nuclear magnetic resonance of hydrogen nuclei (protons) is preferred because of the ubiquity and good NMR characteristics of this nuclear species. However, magnetic resonance of other nuclear and electronic species is useful and so included within the scope of the present invention. In general, the methods of analyzing a fluid according to the invention include introducing a fluid sampling tool into a well bore that traverses an earth formation. The fluid sampling tool extracts the fluid from the earth formation into a flow channel within the tool. While the fluid is in the flow channel, a static magnetic field is applied, and an oscillating magnetic field applied. Magnetic resonance signals are detected from the fluid and analyzed to extract information about the fluid.

These are other features of the invention are described in more detail in figures and in the description below.

Furthermore, a downhole NMR instrument installed in fluid sampling tools can make some of the most important measurements now being made in fluid analysis laboratories. The purpose of the downhole measurements is to provide means of making a partial analysis when the sample is taken, after which the sample can be saved for further analysis or discarded to the borehole. In this manner an unlimited number of fluid samples can be analyzed on each trip in the hole. The measurements are made at formation temperature and pressure, after minimum manipulation, thus helping to ensure sample integrity. Transportation and disposal problems are minimized or eliminated.

Magnetic resonance, e.g., nuclear magnetic resonance (NMR) is a powerful fluid characterization technique. The volumes of individual components of fluid mixtures, and some physical properties of each component, can be measured. The method is inherently noninvasive and noncontacting. Since NMR measurements are volumetric averages, they are insensitive to flow regime, bubble size, and identity of the continuous phase. The method comprises the steps of:

a) obtaining a sample of formation fluid, having an acceptably low level of mud filtrate contamination; p1
b) performing magnetic resonance measurements of the fluid sample to quantitatively determine its physical properties;
c) sending the sample to a sample bottle within the tool for transportation to the surface for further analysis; or
d) discarding the sample to the borehole.

It is therefore an object of this invention to provide an improved method and apparatus for measuring an indication of contamination of fluid samples obtained by downhole tools.

It is another object of the invention to measure various physical properties of formation fluids using magnetic resonance.

BRIEF DESCRIPTION OF THE DRAWINGS

A complete understanding of the present invention may be obtained by reference to the accompanying drawings, when considered in conjunction with the subsequent detailed description, in which.

DESCRIPTION OF THE PREFERRED EMBODIMENT

Apparatus

Figure 1:
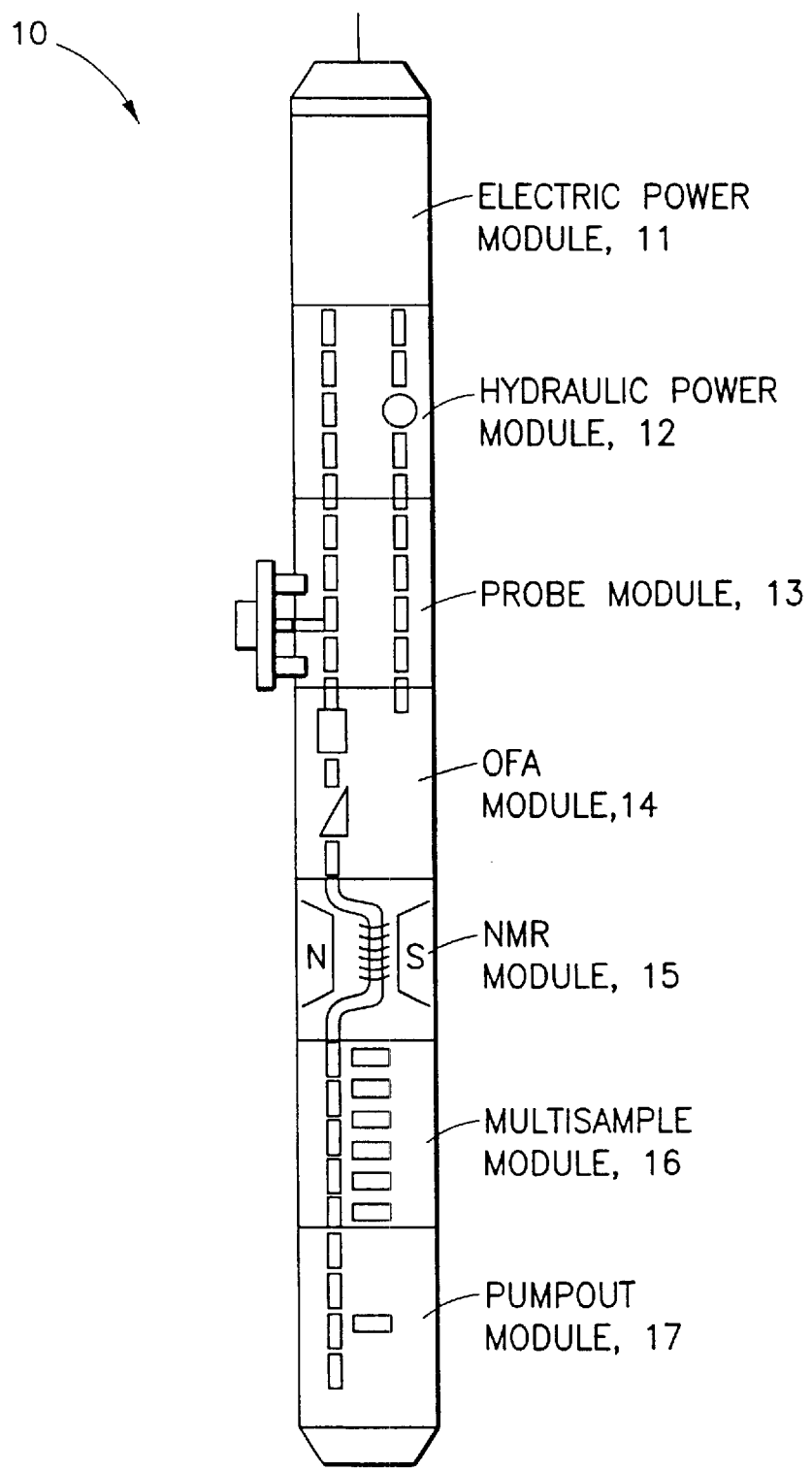
FIG. 1 illustrates a schematic diagram of a fluid sampling tool utitilized in extracting formation fluid in accordance with the invention.

Modern fluid sampling tools, such as Schlumberger's Modular Dynamics Testing Tool (MDT) are composed of several parts which enable extraction of fluids from permeable earth formations. Referring to FIG. 1, with the tool identified by 10, the following modules are in the prior art [*Schlumberger Wireline Formation Testing and Sampling*, SMP-7058 (1996), published by Schlumberger Wireline and Testing]: the electric power module 11 and the hydraulic power module 12 power the tool; the probe module 13 is deployed so as to make a hydraulic seal with the formation; and the pumpout module 17 lowers the pressure in the flow line in a controlled manner so as to extract fluid from the formation while maintaining the pressure near the original formation pressure. Samples are optionally monitored by an optical fluid analyzer (OFA) 14 and are retained for transportation to surface laboratories in the multisample module 16.

The NMR module which is the subject of this invention is shown at 15 in FIG. 1. It is built around the flow line, and provides no obstructions to the flow of fluid within the tool.

Figure 2:
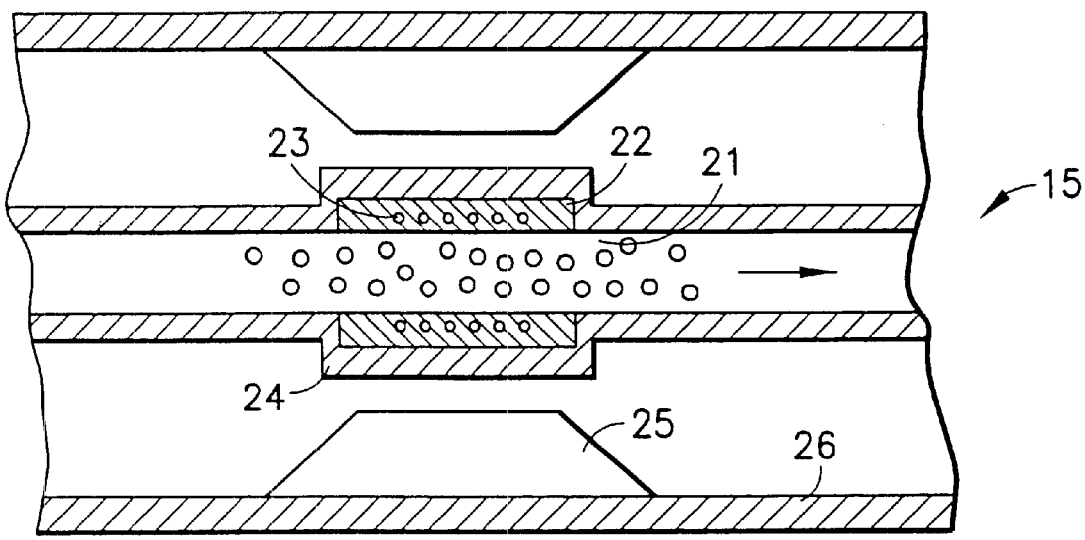
FIG. 2 shows a schematic axial section of a flow line NMR apparatus that can be utilized in the sampling tool depicted in FIG. 1.
Figure 3:
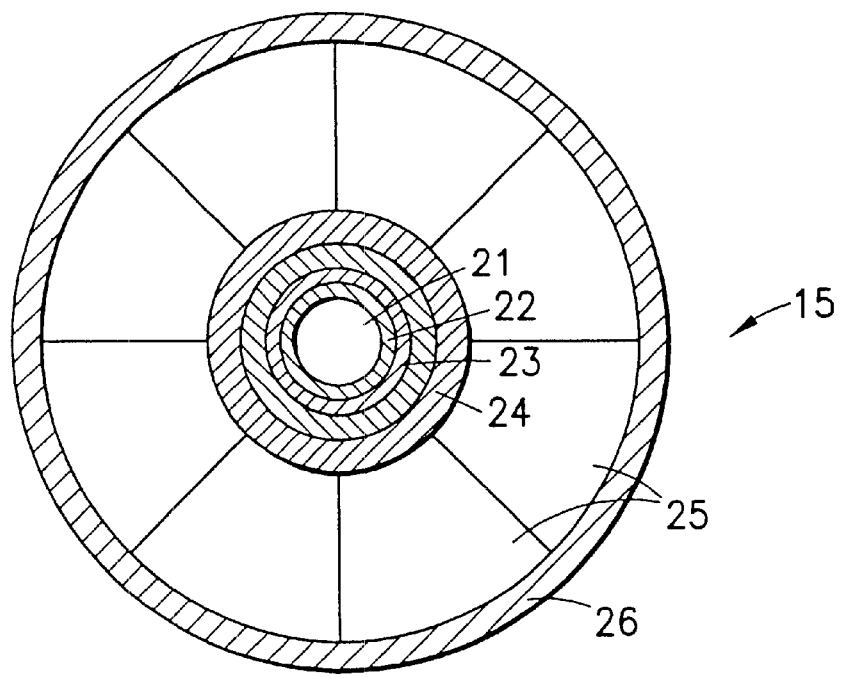
FIG. 3 shows a schematic cross sectional view of a flow line apparatus depicted in FIG. 2.

More detailed drawings of the NMR apparatus 15 are shown in FIGS. 2 and 3. Fluid withdrawn from the formation flows through a flow channel 21. In non-instrumented sections of the tool, the channel is defined by a thick-wall metal tube 24 capable of withstanding formation pressure of at least 20,000 pounds per square inch.

In the NMR-instrumented section of the flow line, the channel is defined by the inside diameter of an antenna support 22. The antenna support must be made of a non-conductive and preferably nonmagnetic material. The antenna support must be capable of resisting chemical attack by formation fluids. It must also be capable of resisting erosion by solids which may enter the flow line from the formation or borehole. Ceramics or hard polymeric materials are suitable materials for the antenna support.

The NMR antenna 23 is embedded in the antenna support. The NMR antenna must be capable of radiating magnetic field at the Larmor frequency (see below), typically 40 MHz. This radiated magnetic field is conventionally called $B_1$. In one illustrative implementation, the NMR antenna is a solenoidal coil which generates an oscillating magnetic field parallel to the axis of the flow channel. The $B_1$ field need not be particularly uniform over the volume of the flow channel.

The antenna support is enclosed by an enlarged portion of thick-wall metal tube 24, so as not to obstruct the flow channel 21. The tube 24 and antenna support 22 are able to contain the high pressure formation fluids in the flow channel. High frequency magnetic fields cannot penetrate metals, so the NMR antenna must be placed inside the metal tube of the flow line.

An array of permanent magnets 25 is placed outside the thick-wall metal tube. These create a constant magnetic field, conventionally called $B_o$, substantially perpendicular to the $B_1$ field generated by the antenna. To make chemical shift measurements (see below) $B_o$ is preferably substantially uniform in the volume occupied by fluid. However, to measure relaxation time, diffusion coefficient, or spin density of hydrogen or other elements, $B_o$ need not be particularly uniform. One suitable arrangement of permanent magnets is described by Halbach [K. Halbach, Nuc. Inst. Methods 169, 1–10 (1980); K. Halbach, Nuc. Inst. Methods 187, 109–117 (1981)].

The entire NMR apparatus is enclosed in a sonde housing 26 which is attached to other similar housings in the tool string lowered into the well.

Gradient coils (not shown) can also be provided for the purpose of making pulsed field gradient measurements of diffusion coefficient and other quantities. If the static magnetic field is aligned with the z-axis, the most effective gradients are $dB_z/dx$, $dB_z/dy$, and $dB_z/dz$. A $dB_z/dz$ gradient can be generated by a pair of saddle coils potted together with the coil which provides the $B_1$ field. Prescriptions for designing saddle coils that generate maximally uniform gradients can be found in the literature [R. Turner, "Gradient Coil Systems", Encyclopedia of Nulear Magnetic Resonance, 1996].

NMR Technique

The techniques of nuclear magnetic resonance are well documented in the literature [E. Fukushima and S. B. W. Roeder, "NMR, A Nuts and Bolts Approach", Addison-Wesley (1981); T. C. Farrar and E. D. Becker, "Pulse and Fourier Transform NMR", Academic Press (1971)]. The static $B_o$ and oscillating $B_1$ magnetic fields should be substantially perpendicular to each other. The $B_1$ antenna should be capable of transmitting and receiving signals at the Larmor frequency f, $$f=(\gamma/2\pi B_o \tag{1}$$

where $\gamma$ is the gyromagnetic ratio of the nuclear species of interest, and Bo is the strength of the static magnetic field. For hydrogen nuclei, $(\gamma/2\pi)=4258$ Hz/Gauss. For values of the gyromagnetic ratio of other nuclei, see e.g. CRC Handbook of Chemistry and Physics [CRC Press], and the Table hereinbelow. Resonating nuclei other than $^1H$ is accomplished by changing the frequency of operation to match the Larmor frequency of the nucleus of interest.

Before quantitative NMR measurements can be made on a fluid sample, it must be exposed to the static magnetic field Bo for a substantial time. The longer the exposure before the measurement begins, the more complete the alignment of nuclear moments by Bo. The degree of alignment, also called polarization, is given by $$P=Po(1-\exp(-t/T_1)) \tag{2}$$

In this equation, t is the time that the nuclei are exposed to Bo before the application of the $B_1$ field, $T_1$ is a time constant characteristic of the material, called the longitudinal relaxation time, P is the degree of polarization, and Po is the degree of polarization in the limit that t goes to infinity. For an explanation of NMR relaxation times, see R. L. Kleinberg and H. J. Vinegar, "NMR Properties of Reservoir Fluids", Log Analyst November-December 1996, pg 20–32. For oil field fluids, $T_1$ can range from a few milliseconds (very viscous crude oils) to 10 seconds (very low viscosity crude oils with dissolved gas).

All standard NMR measurements cain be made using the apparatus described. These include measurement s of spin density (proportional to NMR signal amplitude), longitudinal and transverse relaxation times $T_1$ and $T_2$ and, more generally, their distributions [R. L. Kleinberg, "Well Logging", Encyclopedia of Nuclear Magnetic Resonance, volume 8 pg 4960–4969, John Wiley & Sons, 1996]; diffusion coefficient and other q-space measurements [P. Callaghan, "Principles of Nuclear Magnetic Resonance Microscopy", Clarend on Press, 1991]; flow velocity measurements [A. Capriban and E. Fukushima, "Flow Measurements by NMR", Physics Reports, 198, 195–235 (1990)]; and chemical shift spectroscopy when the $B_o$ field is sufficiently uniform [H. J. Vinegar "Method of Determining Preselected Properties of a Crude Oil", U.S. Pat. No. 5,306, 640 (1994)].

One particularly useful NMR pulse sequence is the Carr-Purcell-Meiboom-Till ("CPMG") pulse sequence, and its generalization, the Fast Inversion Recovery-CPMG pulse sequence [Kleinberg et al, U.S. Pat. No. 5,023,551]. Many other pulse sequences are in common use, as cited in '551, and in the above book references.

Speed Effects

During pumpout, fluid may be moving at a high rate of speed through the flow line NMR apparatus. This limits polarization time and signal acquisition time, so some types of quantitative measurements may not be possible. However, there are a number of methods by which contamination can be monitored qualitatively.

The rate that fluid moves through the tool depends on the permeability of the earth formation, the viscosity of the fluid, and the rate at which fluid can be pumped through the tool. For example, in the Schlumberger MDT, the flow control module allows flows in the range 1–500 $cm^3/s$, while the pumpout module operates at speeds up to about 40 $cm^3/s$. ["Schiumberger Wireline Formation Testing and Sampling" (1996) pg. 4–29, 4–40]. The flow line has an inside diameter of 0.5 cm, so 500 $cm^3/s$ corresponds to a flow speed of 25.5 m/s while 40 $cm^3/s$ corresponds to a flow speed of 2 m/s. The effect of flow is similar to the speed effect of the Schlumberger CMR [J. M. Singer, L. Johnston, R. L. Kleinberg, and C. Flaum, "Fast NMR Logging for Bound Fluid and Permeability", SPWLA 38th Annual Logging Symposium, 1997, Paper YY, Section 3].

Quantitative NMR measurements require that the spins be fully polarized by the static magnetic field prior to data acquisition. This requires that the spins be exposed to Bo for three to five times as long as the longitudinal relaxation time $T_1$. For water or light oils at high temperature, $T_1$ can be several seconds; thus wait times of 10 seconds or more will be required. Since the NMR apparatus is typically 0.3 m long, even moderate flow speeds prevent quantitative measurements from being made during pumpout. However, qualitative measurements to detect contamination can be made during pumpout. When contamination is at a sufficiently low level, pumping can be stopped or slowed and the full range of quantitative measurements are made (see below).

Measurement Overview

Figure 4:
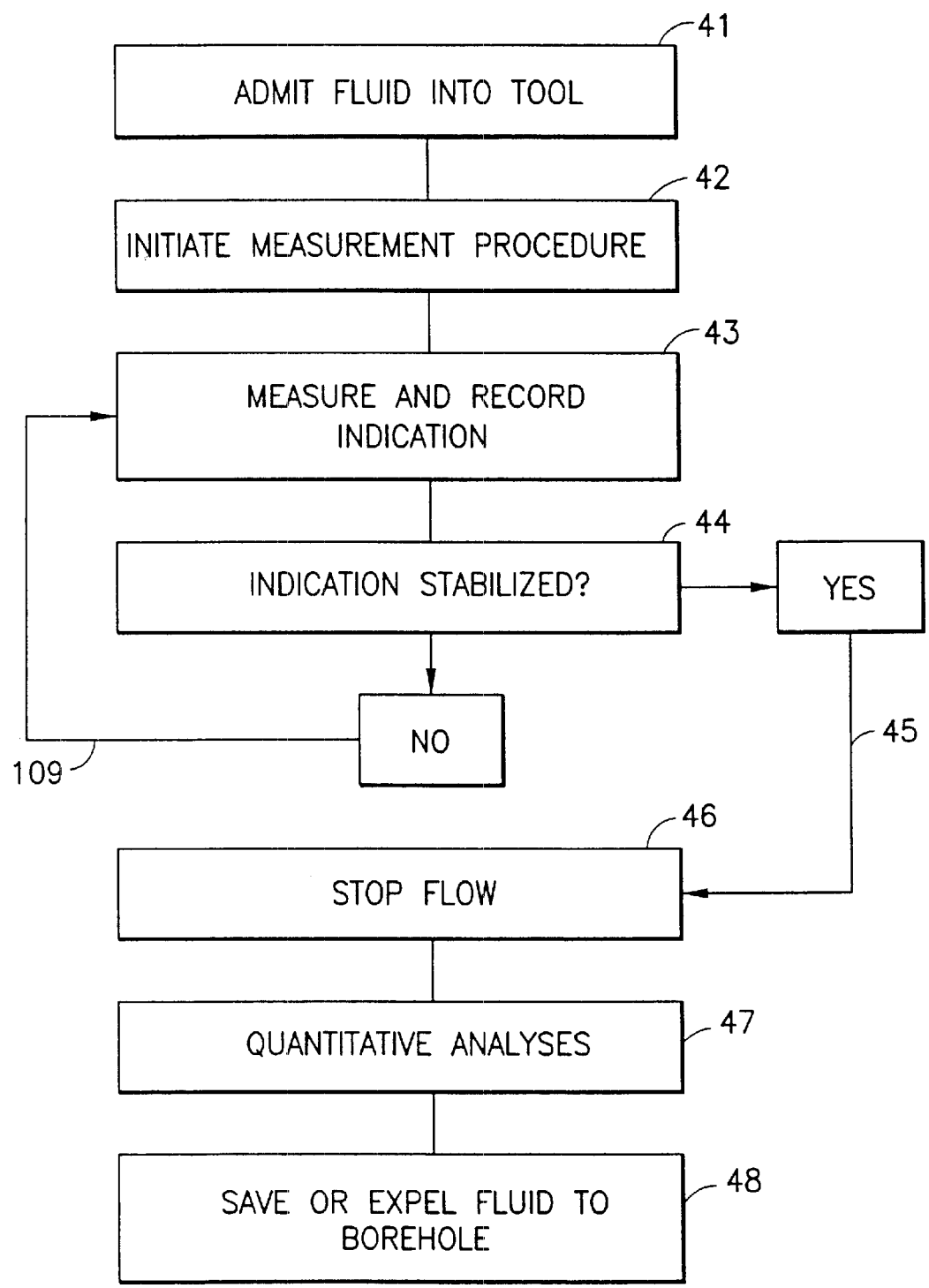
FIG. 4 depicts a flow chart of the method of this invention.

A typical measurement sequence is shown in FIG. 4. Fluid is admitted into the tool flow line 41 and a measurement procedure initiated 42. An indication of magnetic resonance, of a group described below, is measured and recorded 43. While the indication changes with time, the measurement loop is continued 44; when the indication stabilizes 45, contamination has been reduced to a minimum. Then the flow is stopped or slowed 46 and quantative analysis is undertaken 47. At the conclusiof of the quantitative analysis, the fluid in the flow line is routed to storage bottles, or is expelled to the borehole.

There are a wide variety of measurements that can be used to monitor contamination, and another broad group of measurements that are useful in quantitatively analyzing fluid properties. These are described be low.

Contaminiation Monitoig Methods Using Flow Line NMR

Oil Base Mud Filtrate vs. Formation Oil

Many wells are drilled with muds in which oil is the continuous phase. These muds are comprised of hydrocarbons ("base oil"), typically hexadecanes, plus salt water, solids, and chemical additives. Usually only the base oil, together with oil-soluble additives, enter the formnation and mix with formation oils. Water and solids remain in the borehole, or form a filter cake on the borehole wall. The oil entering the formation is called "oil base mud filtrate".

There are a number of NMR-detectable contrasts between oil base mud (OBM) filtrates and formation oils: (1) viscosity, (2) composition, (3) trace element content (natural or introduced), (4) diffusion coefficient, (5) proton density, and (6) molecular conformation.

Figure 5:
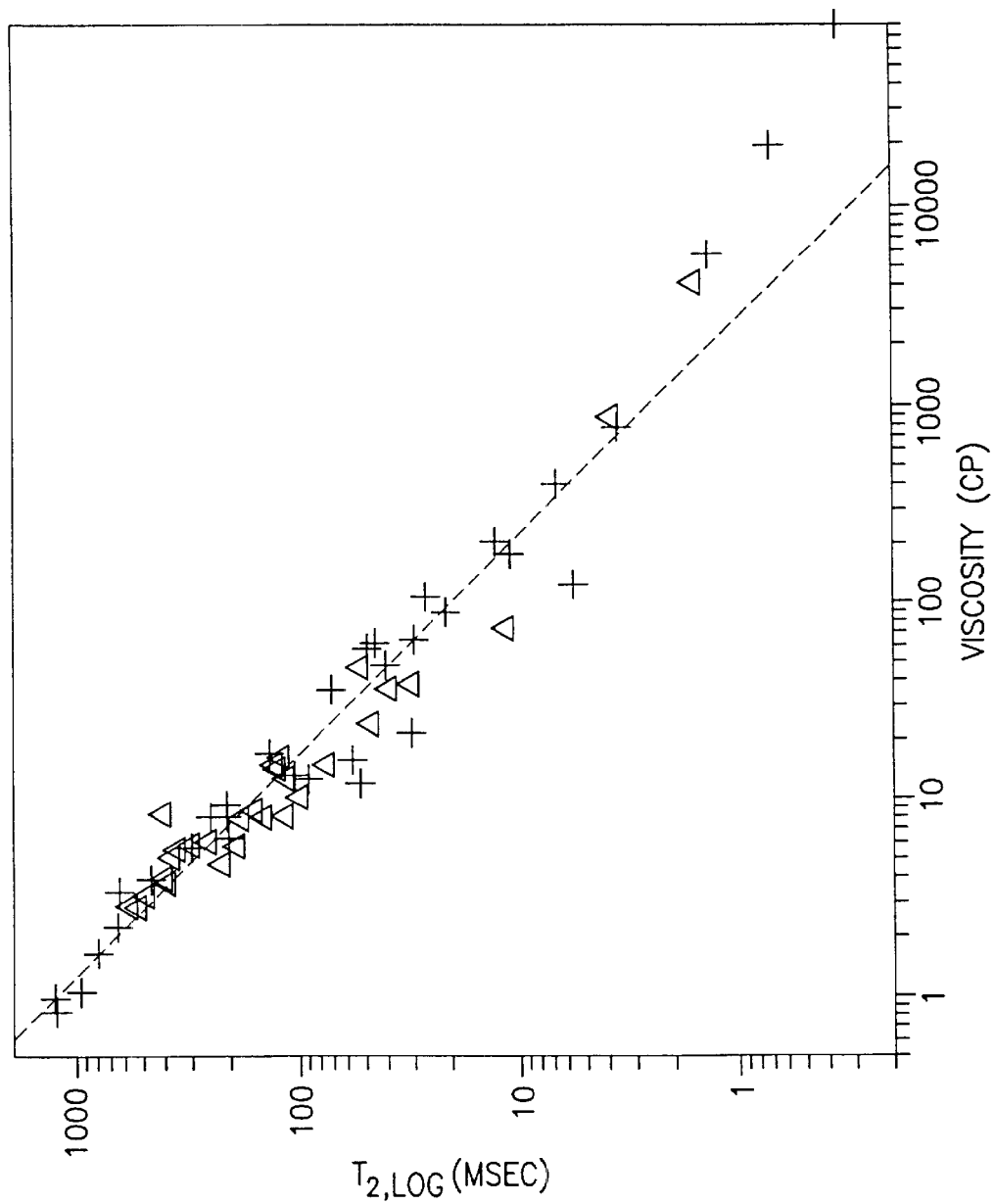
FIG. 5 depicts a graph showing the logarithmic mean $T_2$ plotted versus viscosity for crude oils.

Viscosity: Extensive measurements on pure substances and crude oils have found an excellent correlation between fluid viscosity and the NMR relaxation times $T_1$ and $T_2$ [Bloembergen et al "Relaxation Effects in Nuclear Magnetic Resonance Absorption", Physical Review 73, 679–712 (1948); Morriss et al "Hydrocarbon Saturation and Viscosity Estimation from NwM Logging in the Belridge Diatomite", Log Analyst, Mar-Apr 1997, pg 44–59]. Morriss et al suggest that the logarithmic mean value of the relaxation time is strongly correlated with viscosity, see FIG. 5. Other relaxation time measures are also useful in qualitatively monitoring viscosity, including the time it takes for the NMR amplitude to fall to 1/e of its initial value.

In general, the viscosity of OBM filtrate is different (higher or lower) than that of the formation oil. Thus measurements of NMR relaxation time can distinguish these fluids from one another. Moreover, when OBM filtrate is mixed with formation oil, the viscosity, and therefore relaxation time, of the mixture will be intermediate between the viscosities of the individual components.

As draw down continues, the time dependence of viscosity of the oil phase in the flow stream, $\eta(t)$, will vary as $$\eta(t) = 1\eta_{mf} + [(\eta_n - \eta_{mf})f(t)] \quad (3)$$

where $\eta_{mf}$ is the viscosity of the mud filtrate under downhole conditions, which can be measured in advance in a laboratory if desired, and $\eta_n$ is the unknown viscosity of the native oil. f(t) depends on fluid and formation properties and is therefore unknown. However, f(t) is expected to be subject to the conditions that $f(0) \geq 0$, $df/dt > 0$, $d^2f/dt^2 < 0$ (at least at long time), and $f(\infty) = 1$. Given a sufficiently long acquisition of data, $\eta_n$ can be estimated from the long-time asymptote of $\eta(t)$, and contamination level at any given time can be estimated.

Figure 6:
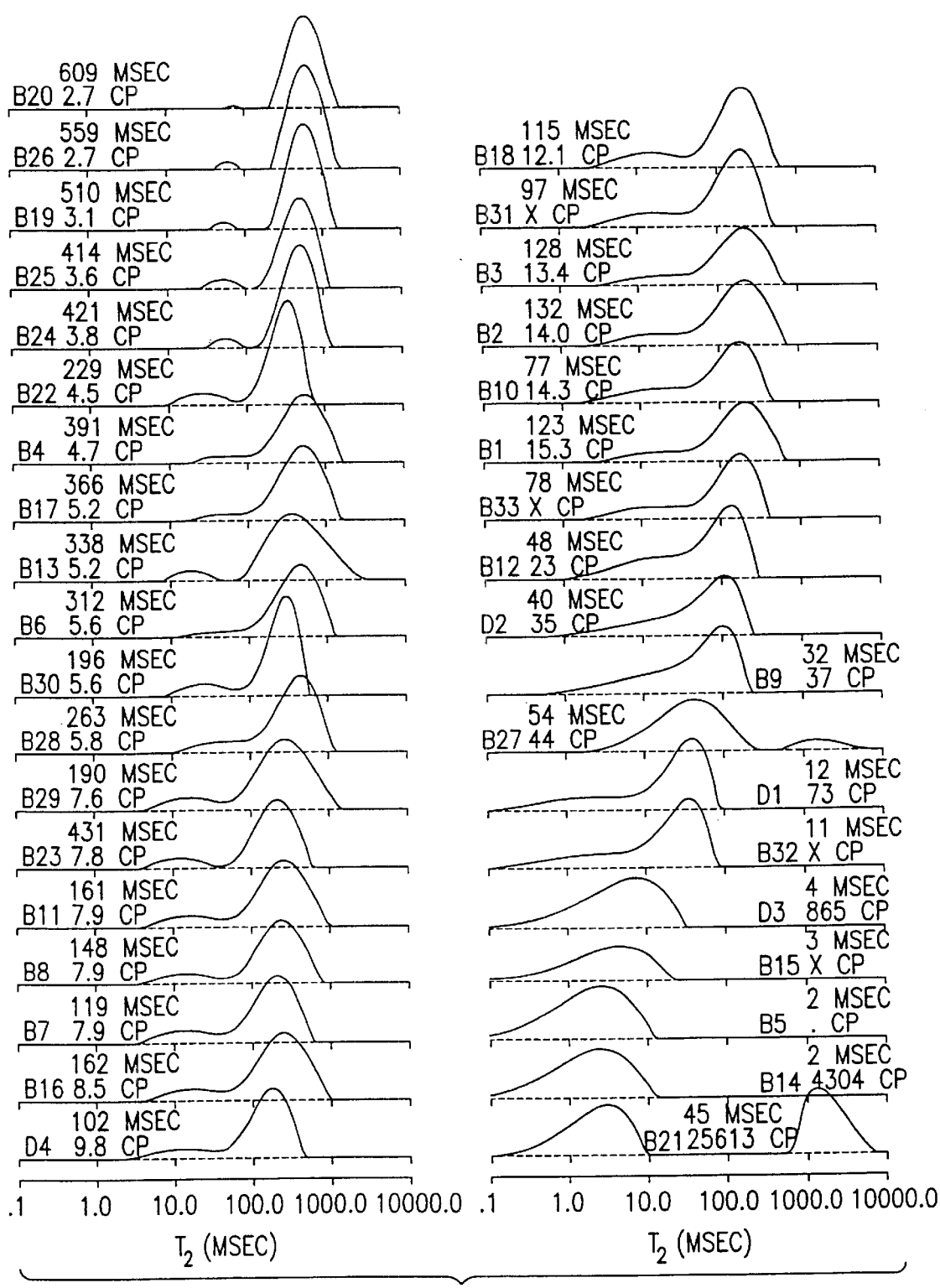
FIG. 6 shows $T_2$ distributions for a number of crude oils having a variety of physical properties.

Relaxation Time Distribution: Oil base mud filtrates are characterized by a narrow distribution of relaxation times. In contrast, crude oils have broad distributions of relaxation times, see FIG. 6 [Morriss et al, "Hydrocarbon Saturation and Viscosity Estimation from NMR Logging in the Belridge Diatomite", Log Analyst, Mar-Apr 1997, pg 44–591]. Thus even if the OBM filtrate and native crude have the same viscosity, NMR $T_2$ analysis can distinguish them based on the width of the distribution of relaxation times.

Trace Element Content: Trace elements can be detected in two ways. (1) Paramagnetic ions or compounds dissolved in liquids shorten the NMR relaxation times of liquid protons. (2) The quantity of certain other nuclear or electronic species can be measured directly by resonance measurements of those species.

Dissolved paramagnetic compounds will reduce the proton relaxation times of oils. Thus if two oils have the same viscosity, they will have different relaxation times if they have substantially different paramagnetic content. While many crude oils and most oil base mud filtrates have negligible magnetic content, some crude oils have significant amounts of vanadium or nickel [Tissot and Welte, "Petroleum Formation and Occurrence", Springer-Verlag, 1978, Figure IV.1.20]. Because the rlaxation effect is proportional to paramagnetic concentration, the proportions of two oils in a mixture can be m onitored. Deliberate introduction of an oil-souble paramagnetic substance into the oil base mud can considerably enhance this effect when the native crude is relativly free of paramagnetic material.

NMR-active nuc lei can be monitored directly to determine contamination levels. OBM filtrates may differ from native oils by having substantiay different concentrations of oxygen, sulfur, or nitrogen. Of these, nitrogen is the best NMR target because its NMR-active form, $^{14}N$, has good NMR sensitivity and a reasonable natural abundance, see Table hereinbelow. Considerably greater sensitivity to contamination can be attained if trace elements are mixed with the drilling mud to mark the filtrate. For example, a fluorine-labeled organic compound can be detected directly by measuring the $^{19}F$ resonance.

Diffusion Coefficient: The diffusion coefficient is closely related to the viscosity; they are related by the approximate relatio n [J. C. M. Li, P. Chang, "Self Diffusion Coefficient and Viscosity in Liquids", J. Chem. Phys. 23, 518–520 (1955)]

$$D_\eta = ckT\left(\frac{N}{V}\right)^{1/3} \quad (4)$$

where D is the diffusion coefficient, $\eta$ is the viscosity, c is an empirical constant, k is Boltzmann's constant, T is the absolute temperature, and (Nar) is the number of molecules per unit volume. Thus in many cases, measurements of $T_2$ and diffusion coefficient are duplicative. However, $T_2$ is influenced by the presence of paramagnetics, whereas the diffusion coefficient is not. Thus diffusion measurements can be independently useful in determining contamination levels.

NMR Amplitude: Speed effects play an important role in the measurement of NMR amplitude, by reducing the time that the nuclear spins are exposed to the polarizing field $B_o$. Hydrogen NMR amplitude is controlled by hydrogen index and the effect of incomplete polarization:

$$S = V_{water} \times HI_{water} \times [1-\exp(-W/T_{1water})] + V_{oil} \times HI_{oil} \times [1-\exp(-W_{1oil})] + V_{gas} \times HI_{gas} \times [1-\exp(-W/T_{1gas})] \quad (5)$$

$V_{water}$, $V_{oil}$, and $V_{gas}$, are the relative volumes of water, oil, and gas in the NMR measurement section of the flow line. HI is the hydrogen index (proton density relative to pure water). W is the polarization time of the measurement, which can be controlled either by the time between pulse sequences, or the flow rate.

Oils with API gravity greater than 20, and with no dissolved gas, have proton density equal to that of water [Vinegar et al, "Whole Core Analysis by 13C NMR", SPE Formation Evaluation 6, 183–189 (June 1991)]. Most oil mud filtrates also have hydrogen densities equal to that of water. Gas is always a formation fluid; it is never a part of mud filtrates. A reduced proton density indicates gas, which is anticorrelated with the presence of mud filtrate in the flow line.

Medium-to-Heavy Oil/Oil Base Mud Filtrate: Medium to heavy oils have short T1, and are substantially polarized in the flow stream. Oil base mud filtrates have $T_1$'s in the range of several hundred milliseconds, and thus are not completely polarized in a rapidly moving stream. As the ratio of heavier formation oil increases, signal amplitude increases.

Light Oil and Gas/Oil Base Mud Filtrate: This is the most important contamination detection problem, and the one the optical fluid analyzer has the most trouble with. In this case, native oil has a longer relaxation time than OBM filtrate. Thus as the proportion of native fluid increases, the proton signal amplitude will decrease. The presence of free gas associated with native oil accentuates the contrast. Signal level will stabilize at a low level when OBM contamination has been eliminated.

Spectroscopy: In ordinary laboratory practice, NMR spectroscopy can be used to distinguish families of hydrocarbons from each other. For example, protons in aromatic (ring) compounds such as benzene and naphthalene, have slightly different resonant frequency than protons in alkanes [H. J. Vinegar "Method of Determining Preselected Properties of a Crude Oil", U.S. Pat. No. 5,306,640 (1994)]. OBM filtrates can be distinguished from formation oils when they have distinctive molecular conformations. Monitoring the spectrum during pumpout provides fluid-selective information. For example, $T_1$ changes in the oil phase can be monitored independent of the signal from water. Incomplete polarization and hydrogen index effects reduce the amplitudes of individual spectral lines. The effects are the same as those affecting the amplitude measurement. Unlike the other techniques discussed, spectroscopy requires very good uniformity of the static magnetic field of the NMR apparatus: typically 1 part per million or better over the sample volume.

Water Base Filtrate vs. Formation Water

Trace Element Content: NMR measurements can also help distinguish water base mud (WBM) filtrate from formation water. There will be little or no contrast in viscosity, diffusion coefficient, proton density, or molecular conformation. However, the trace element content can be considerably different. Water soluble paramagnetic ions (either natural of introduced) will have a strong relaxing effect, which can be used to monitor proportions of filtrate and connate water.

The use of chromium lignosulfonate muds, or manganese tracers used for formation evaluation [Horkowitz et al, 1995 SPWLA Paper Q], add paramagnetic ions to the filtrate. These ions reduce the filtrate relaxation time. Thus they increase contrast with light oils and gas, and decrease contrast with medium to heavy oils.

Paramagnetic ion can also be introduced in the flow line. $2 \times 10^{18}$ ions cm$^3$ of $Fe^{3+}$ will reduce water $T_1$ to 30 msec [Andrew, Nuclear Magnetic Resonance (1955)]. This is equivalent to 54 grams $FeCl_3$ per 100 liters of water. For flow line doping to work, the water must be the continuous phase, and come into contact with the source of ions.

NMR is sensitive to sodium, so if filtrate and connate water have different salinity, sodium concentration provides a good measure of contamination. The flow line apparatus described can make NMR measurements of sodium by retuning the antenna to the appropriate resonance frequency. Sodium longitudinal relaxation time is 47 ms at 2 MHz and room conditions. Thus the amplitude of the sodium resonance can be measured at least semi-quantitatively during flow.

Potassium is particularly interesting because of its large concentration in KCl muds. Monitoring potassium NMR amplitude is a direct measure of contamination when KCl mud has been used. The longitudinal relaxation time of potassium in aqueous solution is 38 msec [Decter, Progress in Inorganic Chemistry 29, 285 (1982)] so speed effect is minor.

Oil vs. Water

Oil and water can be distinguished by many of the same techniques outlined above. Proton relaxation time differences may be based on viscosity, diffusion coefficient, paramagnetic relaxation agents, or NMR-visible trace elements. The water phase will have a very narrow relaxation time distribution in contrast to crude oil, which often has a broad distribution. Salt water has a large sodium and/or potassium NMR signal which will be absent in the oil phase. Chemical shift spectroscopy can separate oil and water resonances.

NMR Amplitude: Medium-to-Heavy OiL/Water Base Mud Filtrate: The more viscous the oil, the more completely it will be polarized, because viscous oils relax quickly and flow slowly (at least in some flow regimes). In contrast, the viscosity of produced water is less than 1 centipoise, and frequently has a long relaxation time $T_1$. Thus the oil will be fully polarized and the water will not. As contamination is reduced, the signal gets bigger.

Light Oil and Gas/Water Base Mud Filtrate: The presence of formation gas depresses the total signal as water contamination diminishes.

Electron Spin Resonance

Electron spin resonance (ESR) is useful because of its great sensitivity to unpaired electron spins, even at very low spin density. Unpaired electrons are found in naturally occurring or artificially introduced magnetic transition metal ions such as iron, manganese, chromium, cobalt, vanadium and nickel. These last two are frequently found in crude oils. Chromium is found at high concentration in a number of water base mud filtrates. Natural ground water has significant iron content. In general, mud filtrates and formation fluids will have different concentrations of transition metal ions, so ESR can be used to monitor the relative concentrations of filtrate and native fluids.

Unpaired electrons are also present in the free radicals of certain hydrocarbons, tertiary alkanes and alkyl benzenes, for example [Morrison and Boyd, Organic Chemistry, Allyn and Bacon, 1973]. The density of free radicals can be increased artificially by irradiating hydrocarbons with a low-level radioactive source located in the flow line upstream of the ESR cell. This can provide contrast between OBM filtrates and formation oils, which are likely to have differing amounts of compounds in which free radicals are stable.

ESR apparatus is similar to NMR apparatus. They use the same magnet, or separate ones of similar design. Because ESR resonance frequencies are abut 700 times higher than proton NMR frequencies, a microwave resonator is needed to provide the $B_1$ field.

Figure 7:
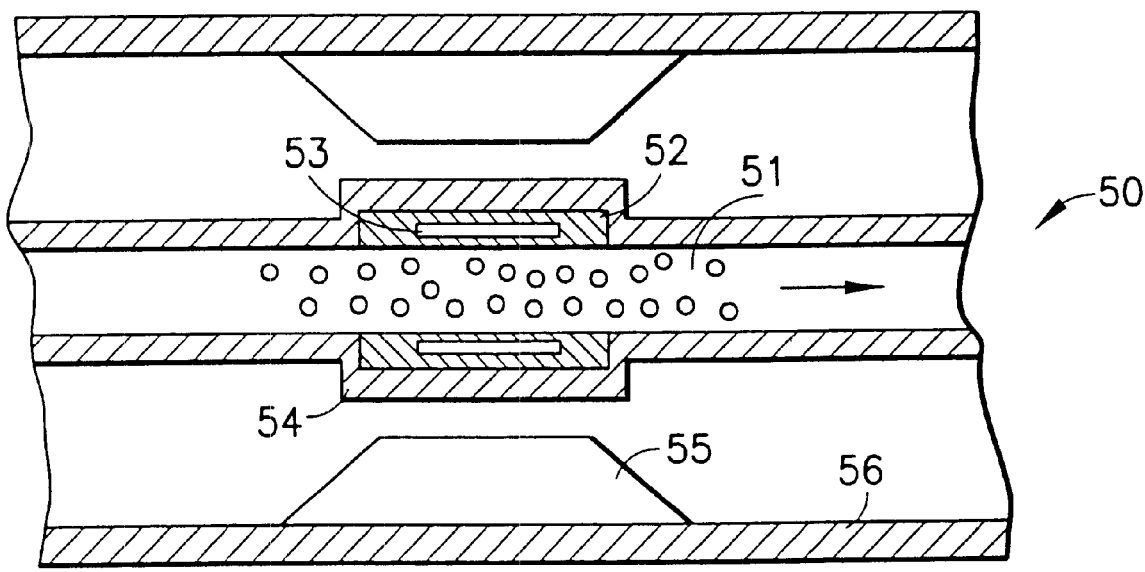
FIG. 7 shows an axial section of a flow line ESR apparatus that can be utilized in the sampling tool depicted in FIG. 1.

The ESR module, which is another aspect of this invention, replaces or supplements the NMR module heretofore discussed and shown at 15 in FIG. 1. Like the NMR module, the ESR module is built around the flow line, and provides no obstructions to the flow of fluid within the tool. A more detailed drawing of the ESR apparatus is shown at 50 in FIG. 7.

Fluid withdrawn from the formation flows through a flow channel 51. In non-instrumented sections of the tool, the channel is defined by a thick-wall metal tube 54 capable of withstanding formation pressure of at least 20,000 pounds per square inch.

In the ESR-instrumented section of the flow line, the channel is defined by the inside diameter of a resonator support 52. The resonator support must be made of a nonconductive and preferably nonmagnetic material. It should also have low dielectric loss at the frequency of operation. The resonator support must be capable of resisting chemical attack by formation fluids. It must also be capable of resisting erosion by solids which may enter the flow line from the formation or borehole. Many ceramics or hard polymeric materials are suitable materials for the resonator support.

The ESR resonator 53 is embedded in the resonator support. The ESR resonator must be capable of radiating magnetic field at the electron resonance frequency, typically in the microwave (gigahertz) frequency range. In one illustrative implementation, the ESR resonator is a cylindrical microwave cavity operated in the $TE_{111}$ mode. Such cavities, their modes, and the electronics used to operate them, are described in, e.g. W. Low, "Paramagnetic Resonance in Solids", New York: Academic Press (1960), pg 180–193.

The resonator support is enclosed by an enlarged portion of thick-wall metal tube 54, so as not to obstruct the flow channel 51. The tube 54 and resonator support 52 are able to contain the high pressure formation fluids in the flow channel. High frequency magnetic fields cannot penetrate metals, so the ESR resonator must be placed inside the metal tube of the flow line.

An array of permanent magnets 55 is placed outside the thick-wall metal tube. These create a constant magnetic field, conventionally called $B_o$, substantially perpendicular to the magnetic field generated by the resonator. One suitable arrangement of permanent magnets is described by Halbach [K. Halbach, Nuc. Inst. Methods 169, 1–10 (1980); K. Halbach, Nuc. Inst. Methods 187, 109–117 (1981)].

The entire ESR apparatus is enclosed in a sonde housing 56 which is attached to other similar housings in the tool string lowered into the well.

Quantitative Fluid Characterization with NMR

A downhole NMR instrument installed in fluid sampling tools can make some of the most important measurements now being made in fluid analysis laboratories. The purpose of the downhole measurements is to provide means of making a partial analysis when the sample is taken, after which the sample can be saved for further analysis or discarded to the borehole. In this manner an unlimited number of fluid samples can be analyzed on each trip in the hole. The measurements are made at formation temperature and pressure, after minimum manipulation, thus helping to ensure sample integrity. Transportation and disposal problems are minimized or eliminated.

Nuclear magnetic resonance (NMR) is a powerful fluid characterization technique. The volumes of individual components of fluid mixtures, and some physical properties of each component, can be measured. The method is inherently noninvasive and noncontacting. Since NMR measurements are volumetric averages, they are insensitive to flow regime, bubble size, and identity of the continuous phase.

The physical properties of formation fluid are determined quantitatively by making a measurement w hen it has been determined tha t contamination is reduced to an acceptable level. Alternatively, fluids can be characterized by measuring their physical properties during mud filtrate clean up, and extrapolating the results to zero contamination level.

Nuclear magnetic resonance of $^1H$ (protons) is preferred because of the ubiquity and good NMR characteristics of this nuclear species. However, magnetic resonance of other nuclear species are useful and can be performed by the same apparatus, as detailed below. The apparatus and technique are the same as described above.

Volume Fractions

The calibrated NMR signal from a mixture of gas, oil, and water is $$S=V_{water} \times HI_{water} \times [1-\exp(-W/T_{1water})]+V_{oil} \times HI_{oil} \times [1-\exp(-W/T_{oil})]+V_{gas} \times HI_{gas} \times [1-\exp(-W/T_{1gas})] \qquad (6)$$

$V_{water}$, $V_{oil}$ and $V_{gas}$ are proportional to the volumes of each fluid. HI (hydrogen index) is the proton density for each fluid, normalized to the proton density of water at 20° C. and 1 atmosphere pressure. The last factor on each line is a correction to account for insufficient polarization time W.

Water, oil, and gas signals ca n be separated by methods describ ed below. To obtain the fluid volumes from resolved NMR signals, the hydrogen index must be determined. The situation is different for each fluid. For charts of hydrogen index, see R. L. Kleinberg, H. J. Vinegar, Log Analyst, Nov.-Dec. 1996, pg. 20–32.

Water. $HI_{water}$ is defined to be unity at room temperature and pressure; the effects of elevated temperature and pressure are tabulated [Amyx, Bass and Whiting, Petroleum Reservoir Engineering, 1960, pg 458]. A larger correction to $HI_{water}$ is due to salinity. Thus the salt content of the water must be known to obtain an accurate volune. The solubility of natural gas in water is low, and therefore does not have a significant effect on hydrogen index.

Oil: For oil at room temperature and pressure, without dissolved gas, hydrogen index is unity for API gravity greater than 20 [H. J. Vinegar et al, "Whole Core Analysis by 13C NMR", SPE Formation Evaluation, 6, 183–189 (1991)], which is the range of interest for fluid sampling tools. $HI_{oil}$ will track density as a function of temperature and pressure. There is no generally accepted correlation between $HI_{oil}$ and dissolved gas content.

Gas: $HI_{gas}$ is in the range of 0–0.6 for oilfield conditions, so the gas signal is not negligible. $HI_{gas}$ is a known function of temperature and pressure, which are measured by fluid sampling tools, and chemical composition, which is not. Carbon dioxide has no proton NMR signal, and thus may be obtained by difference when the volumes of water, oil, and natural gas are measured directly.

Relaxation Time Analysis

Water and Oil in the Absence of Gas: Water in the tool flow line at downhole temperature and pressure will have relaxation times of several seconds. The magnetization decay of crude oils is multiexponential, but when the downhole viscosity of oil is greater than a few centipoise, water and oil NMR signals have distinctly different relaxation times [R. L. Kleinberg, H. J. Vinegar, Log Analyst, Nov.-Dec. 1996, pg. 20–32.]. This enables oil and water signals to be separated using a $T_2$ distribution, as is familiar from NMR formation evalua tion [R. L. Kleinberg and C. Flaum, "Review: NMR Detection and Characterization of Hydrocarbons in Subsurface Earth Formations", in "Spatially Resolved Magnetic Resonance: Methods and Applications in Materials Science, Agriculture and Biomedicine", B. Blumich, et al eds, 1998]. If the water and oil signals are well resolved in the $T_2$ distribution, in the absence of free gas, the areas under the peaks are equal to $$V_{water} \times HI_{water} \times [1-\exp(-W/T_{1water})] \qquad (7a)$$

and $$V_{oil} \times HI_{oil} \times [1-\exp(-W/T_{1oil})] \qquad (7b)$$

respectively. $T_1=T_2$ for liquids in the flow line apparatus, so if $T_2$ is measured by the CPMG pulse sequence, the polarization correction can be accurately computed.

Gas Measurements: The relaxation time of gas is a function only of its temperature and pressure, which are measured. For free gas in the absence of magnetic field gradients, $T_1=T_2$, in the range of several seconds, and the decay is single exponential [C. Straley, "An Experimental Investigation of Methane in Rock Materials", SPWLA 38th Annual Logging Symposium, 1997, Paper AA]. Thus the decay time of free gas can coincide with water and light oil. Gas is distinguished from liquids by its diffusion coefficient. Several methods may be used:

Gas Diffusion-Relaxation Method 1:
(1) The transverse magnetization decay is measured by CPMG in the usual manner, and the $T_2$ distribution is determined. Gas relaxes with relaxation time $T_{2,bulk}$.
(2) The transverse magnetization decay is measured by CPMG in the presence of a uniform, steady magnetic field gradient supplied by gradient coils. The relaxation rate of gas is then $$\frac{1}{T_2} = \frac{1}{T_{2,bulk}} + \frac{(\gamma G T_E)^2 D}{12} \qquad (8)$$

where $\gamma$ is the gyromagnetic ratio, G is thee applied gradient, $T_E$ is the CPMG echo spacing, and D is the diffusion coefficient. Since $T_{2,bulk}$ and all these parameters are known, the two measurements can be readily analyzed for the gas signal.

Gas Diffusion-Relaxation Method 2:
A pulsed field gradient technique can be used, analogous to that described by Kleinberg, Latoupr and Sezginer, U.S. patent application Ser. No. 08/783,778.

Chemical Shift Analysis: Proton NMR chemical shift can also be used to distinguish fluids [H. J. Vinegar, U.S. Pat. No. 5,306,640 (1994)]. Gas, light oil, and water have distinct chemical shifts [Dyer, Applications of Absorption Spectroscopy of Organic Compounds (1965) pg. 84–85.]

|            | TMS | $CH_4$ | $H_3C-C$ | $-CH_2-$ | $H_2O$ |
|------------|-----|--------|----------|----------|--------|
| Shift (ppm) | 10  | 9.77   | 9.1      | 8.7      | 4.7    |

The chemical shift of methane depends on pressure [Trappeniers and Oldenziel, Physica 82A, 581 (1976)], and whether it is in the gas phase or in solution [Rummens and Moutits, Canadian Journal of Chemistry 55, 3021 (1977)].

Fluids are distinguished when the $B_o$ measurement field is homogeneous to better than 1 part per million. The areas under the spectral lines are proportional to fluid volumes as described by Eqn (6). Chemical shift spectroscopy is particularly useful when oil and water have similar relaxation times.

Carbon NMR
Carbon may be found in some formation waters, as carbonate or bicarbonate ion, but it predominates in oil and gas. Thus in many cases, a measurement of carbon amplitude gives a direct measurement of hydrocarbon quantity. The NMR-active isotope of carbon is $^{13}C$, which has a natural abundance of about 1%. Cross-polarization techniques increase signal to noise ratio [Gerstein and Dybowski, Transient Techniques in NMR of Solids, 1985].

Oil Viscosity
Oil viscosity can be determined if the oil signal is resolved from other fluid signals by either relaxation analysis (see above) or chemical shift analysis (see above).

When relaxation analysis is used, $T_2$ is measured directly. As stated above, crude oils have broad distributions of relaxation times. However, it has been found that oils with low viscosity relax more slowly than those with higher viscosity [C. E. Morriss, R. Freedman, C. Straley, M. Johnston, H. J. Vinegar, P. N. Tutunjian, in Transactions of the SPWLA 35th Annual Logging Symposium, 1994; Log Analyst, March-April 1997, pg 44.]. A single relaxation time parameter which captures the viscosity dependence is the logarithmic mean $T_2$:

$$T_{2LM} = \exp\left[\frac{\sum_i m_i \log_e(T_{2i})}{\sum_i m_i}\right] \qquad (9)$$

It has been found that over the range 1 cp to 300 cp, and in the absence of an applied magnetic field gradient, $T_{2LM}$ (in seconds) is related to viscosity $\eta$ (in centipoise)

$$T_{2LM} = \frac{1.2}{\eta^{0.9}} \qquad (10)$$

When chemical shift analysis is used, the longitudinal relaxation time, $T_1$, of each spectral line can be determined by standard methods [H. J. Vinegar U.S. Pat. No. 5,306,640 (1994)]. Then viscosity can be found from Eqn (5) using the fact that $T_1=T_2$ for crude oils in the absence of magnetic field gradients.

Oil Composition
One of the primary products of conventional fluid analysis is oil composition. There are two methods by which NMR can provide at least a partial composition analysis: spectroscopy and relaxation time analysis.

Spectroscopy: The NMR chemical shift depends on the molecular environment of a spin. Thus chemical conformation can be determined; this is one of the oldest and most widespread uses of nuclear magnetic resonance. Crude oils are complex mixtures of hydrocarbons, and NMR spectroscopy is used to identify characteristic bands. For example, aliphatic protons appear in one frequency band, while aromatic protons appear at another; both are distinguishable from water [H. J. Vinegar, U.S. Pat. No. 5,306,640 (1994)]. Chemical shift spectroscopy can performed using either $^1H$ or $^{13}C$ [Petrakis and Edelheit, Applied Spectroscopy Reviews 15, 195 (1979); Botto, "Fossil Fuels", Encyclopedia of Nuclear Magnetic Resonance (1996)].

Relaxation Time Analysis: The relaxation time depends on correlation times due to molecular motion [Bloembergen, Purcell and Pound, Physical Review 73, 679 (1948)]. Protons in large molecules tend to move slower, and hence relax faster, than those in small molecules. Crude oils are mixtures of pure hydrocarbons, and have broad distributions of relaxation times [C. E. Morriss, R. Freedman, C. Straley, M. Johnston, H. J. Vinegar, P. N. Tutunjian, in Transactions of the SPWLA 35th Annual Logging Symposium, 1994; Log Analyst, March-April 1997, pg 44]. Oil type is determined by comparing relaxation time distributions obtained in the fluid sampling tool to a catalogue of such distributions compiled from laboratory data.

Water Phase Salinity
Determination of oil saturation from deep resistivity measurements requires knowledge of the water resistivity, $R_W$. The present resistivity measurement implemented in fluid sampling tools is a low-frequency current injection technique, which is unable to measure $R_W$ in the presence of hydrocarbon.

It is possible to estimate $R_W$ by measuring the concentration of current-carrying ions. The common ions in reservoir waters are ["Petroleum Engineering Handbook", H. B. Bradley, ed., Society of Petroleum Engineers, 1992, Chapter 24]:
cations: Ca, Mg, Na
anions: $CO_3$, $HCO_3$, $SO_4$, Cl
Among the cations, sodium often dominates, but there can be significant quantities of calcium and magnesium in some areas. Chlorine usually dominates anion m concentration, although there are some areas where carbonate, bicarbonate, or sulfate are important.

Solubility limits the combinations of ions that can be present simultaneously [CRC Handbook of Chemistry and Physics, pg B-73 et seq.]. Note that solubilities can be modified by acidity, and depend on temperature.
Relatively soluble combinations:

| Cation | Anion | Solubility (g/l) (hot water) |
|---|---|---|
| Na | Cl | 391 |
| Na | $CO_3$ | 455 |
| Na | $SO_4$ | 425 |
| Ca | Cl | 1590 |
| Mg | Cl | 727 |
| Mg | $SO_4$ | 738 |

Relatively insoluble combinations:

| Cation | Anion | Solubility (g/l) (hot water) |
|---|---|---|
| Ca | $CO_3$ | 0.019 |
| Ca | $SO_4$ | 0.162 |
| Mg | $CO_3$ | 0.106 |

Thus high concentrations of calcium are incompatible with high levels of carbonate or sulfate, while high levels of magnesium are incompatible with high levels of carbonate. The magnesium sulfates (epsomite, kieserite) are not particularly common minerals, and magnesium and sulfate ion are rarely seen together at high concentrations [Petroleum Engineering Handbook, Chapter 24]. Thus measuring sodium and chloride, and applying the condition of charge neutrality, constrains the composition of oilfield waters. "Sodium waters" are those brines which have an excess of sodium over chloride:

$$[Na^+]-[Cl^-]=2([CO_3^{--}]+[SO_4^{--}]) \text{ for } [Na^+]-[Cl^-]>0 \quad (11)$$

"Chloride waters" are those brines which have an excess of chloride over sodium:

$$[Cl^-]-[Na^+]=2([Ca^{++}]+[Mg^{++}]) \text{ for } [Cl^-]-[Na^+]>0 \quad (12)$$

Thus total salinity (maximum of $[Na^+]$ and $[Cl^-]$) and an estimate of ion identity can be obtained, and used to estimate hydrogen index (see above), and water conductivity. The salinity is also important in estimating parameters for determination of density by gamma ray scattering or X-ray scattering.

By changing the operating frequency of the NMR apparatus, the quantities of various isotopes can be determined. NMR properties of commonly occurring elements in oilfield fluids may be found in the Table hereinbelow. The best isotopes for NMR measurements are $^1H$, $^{23}Na$ and $^{35}Cl$. The NMR amplitude of the sodium or chlorine resonance will give the volume of water multiplied by the concentration of the ion.

TABLE

NMR Properties of Elements Common in Oilfield Fluids

| Isotope | Frequency Frequency ($^1H$) | Natural Abundance | NMR Sensitivity[1] | Net Sensitivity[2] |
|---|---|---|---|---|
| $^1H$ | 1 | 1.00 | 1 | 1 |
| $^{13}C$ | 0.251 | 0.011 | $1.59 \times 10^{-2}$ | $1.75 \times 10^{-4}$ |
| $^{17}O$ | 0.136 | $3.7 \times 10^{-4}$ | $2.91 \times 10^{-2}$ | $1.08 \times 10^{-5}$ |
| $^{23}Na$ | 0.264 | 1.00 | $9.25 \times 10^{-2}$ | $9.25 \times 10^{-2}$ |
| $^{25}Mg$ | 0.061 | 0.101 | $2.67 \times 10^{-3}$ | $2.70 \times 10^{-4}$ |
| $^{33}S$ | 0.076 | 0.0076 | $2.26 \times 10^{-3}$ | $1.72 \times 10^{-5}$ |
| $^{35}Cl$ | 0.098 | 0.755 | $4.70 \times 10^{-3}$ | $3.55 \times 10^{-3}$ |
| $^{37}Cl$ | 0.082 | 0.245 | $2.71 \times 10^{-3}$ | $6.63 \times 10^{-4}$ |
| $^{39}K$ | 0.047 | 0.931 | $5.08 \times 10^{-4}$ | $4.74 \times 10^{-4}$ |

[1]At 100% abundance, $^1H = 1$
[2]At natural abundance, $^1H = 1$

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

I claim:

1. A method of analyzing a fluid in a downhole environment comprising:
    a) introducing a fluid sampling tool into a well bore that traverses an earth formation;
    b) using the fluid sampling tool to extract the fluid from the earth formation into a flow channel within the tool;
    c) applying a static magnetic field to the fluid in the flow channel;
    d) applying an oscillating magnetic field to the fluid in the flow channel;
    e) detecting magnetic resonance signals from the fluid;
    f) analyzing the detected magnetic resonance signals to extract information about the fluid.

2. The method of claim 1, further comprising flowing the fluid through the flow channel and performing steps (c)–(e) while the fluid is flowing.

3. The method of claim 1, further comprising flowing the fluid through the flow channel and slowing the flow of the fluid through the flow channel during steps (c)–(e).

4. The method of claim 1, further comprising flowing the fluid through the flow channel and stopping the fluid in the flow channel during steps (c)–(e).

5. The method of claim 4, wherein analyzing the detected magnetic resonance signals comprises performing a chemical shift analysis.

6. The method of claim 1, wherein the static magnetic field is substantially perpendicular to the oscillating magnetic field.

7. The method of claim 1, wherein analyzing the detected magnetic resonance signals comprises detecting an indication of a contaminant in the fluid.

8. The method of claim 7, wherein the indication of the contaminant comprises one of the following: viscosity, relaxation time, composition, trace element content, diffusion coefficient, proton density, and molecular conformation.

9. The method of claim 7, wherein the contaminant comprises a drilling mud filtrate.

10. The method of claim 7, further comprising monitoring the indication of the contaminant to determine when the contaminant has been substantially eliminated from the fluid.

11. The method of claim 1, further comprising applying a magnetic field gradient to the fluid in the flow channel.

12. The method of claim 11, wherein analyzing the detected magnetic resonance signals comprises determining an indication of diffusion.

13. The method of claim 12, wherein applying the magnetic field gradient comprises applying magnetic field gradient pulses to the fluid in the flow channel.

14. The method of claim 1, wherein step (d) comprises applying a sequence of oscillating magnetic field pulses to the fluid in the flow channel.

15. A method of analyzing a fluid comprising:
   a) introducing a fluid sampling tool into a well bore that traverse an earth formation;
   b) using the fluid sampling tool to extract the fluid from the earth formation into a flow channel in the tool;
   c) applying a static magnetic field to the fluid in the flow channel;
   d) applying an oscillating magnetic field to the fluid in the flow channel;
   e) detecting nuclear magnetic resonance signals from the fluid, the nuclear magnetic resonance signals resulting from an interaction between nuclear spins in the fluid and the static and oscillating magnetic fields; and
   f) analyzing the detected nuclear magnetic resonance signals to extract information about the fluid.

16. The method of claim 15, wherein applying the oscillating magnetic field comprises applying an oscillating magnetic field at a Larmor frequency.

17. The method of claim 15, wherein applying the oscillating magnetic field comprises applying an oscillating magnetic field at a frequency sensitive to hydrogen nuclei.

18. The method of claim 15, wherein analyzing the detected nuclear magnetic resonance signals comprises determining a relaxation time.

19. The method of claim 15, wherein analyzing the detected nuclear magnetic resonance signals comprises determining a relaxation time distribution.

20. The method of claim 15, wherein analyzing the detected nuclear magnetic resonance signals comprises determining an indication of diffusion.

21. The method of claim 15, wherein analyzing the detected nuclear magnetic resonance signals comprises determining an indication of fluid viscosity.

22. The method of claim 15, wherein analyzing the detected nuclear magnetic resonance signals comprises detecting presence of a contaminant in the fluid.

23. The method of claim 15, wherein analyzing the detected nuclear magnetic resonance signals comprises detecting presence of a paramagnetic species in the fluid.

24. A method of analyzing a fluid comprising:
   a) introducing a fluid sampling tool into a well bore that traverse an earth formation;
   b) using the fluid sampling tool to extract the fluid from the earth formation into a flow channel in the tool;
   c) applying a static magnetic field to the fluid in the flow channel;
   d) applying an oscillating magnetic field to the fluid in the flow channel;
   e) detecting electron spin resonance signals from the fluid, the electron spin resonance signals resulting from an interaction between electron spins in the fluid and the static and oscillating magnetic fields; and
   f) analyzing the detected electron spin resonance signals to extract information about the fluid.

25. The method of claim 24, wherein applying the oscillating magnetic field comprises applying an oscillating magnetic field at a microwave frequency.

26. The method of claim 24, wherein analyzing the detected electron spin resonance signals comprises detecting an indication of contamination in the fluid.

27. The method of claim 26, wherein the indication of contamination comprises a transition metal ion.

28. The method of claim 26, wherein the indication of contamination comprises a free radical.

29. The method of claim 26, wherein analyzing the detected electron spin resonance signals further comprises determining a relative concentration of contamination in the fluid.

30. An apparatus for analyzing a fluid in a downhole environment comprising:
   means for extracting the fluid from an earth formation into a flow channel within a well logging tool;
   means for generating a static magnetic field within the flow channel;
   means for generating an oscillating magnetic field within the flow channel that is substantially perpendicular direction to the static magnetic field;
   means for detecting magnetic resonance signals; and
   means for analyzing the detected magnetic resonance signals.

31. The apparatus of claim 30, wherein the means for generating the static magnetic field comprises a permanent magnet.

32. The apparatus of claim 30, wherein the means for generating the static magnetic field comprises an array of permanent magnets.

33. The apparatus of claim 30, wherein the means for generating the oscillating magnetic field comprises a nuclear magnetic resonance antenna.

34. The apparatus of claim 33, wherein the means for detecting magnetic resonance signals comprises the nuclear magnetic resonance antenna.

35. The apparatus of claim 30, wherein the means for generating the oscillating magnetic field comprises a microwave generator.

36. The apparatus of claim 30, wherein the flow channel defines a flow axis and the means for generating the static magnetic field generates the static magnetic field in a direction substantially perpendicular to the flow axis.

37. The apparatus of claim 30, wherein the flow channel defines a flow axis and the means for generating the oscillating magnetic field generate the oscillating magnetic field in a direction substantially parallel to the flow axis.

38. The apparatus of claim 30, further comprising means for generating magnetic field gradient pulses.

39. A well logging tool comprising:
   a pumpout module;
   means defining a channel that is in fluid connection with the pumpout module;
   an array of permanent magnets arranged around the channel to generate a static magnetic field within the channel; and
   a nuclear magnetic resonance (NMR) antenna arranged around the channel to generate an oscillating magnetic field within the channel.

40. The tool of claim 39, wherein the means defining the channel comprises an antenna support in which the NMR antenna is embedded.

41. The tool of claim 40, wherein the antenna support comprises a nonconductive material.

42. The tool of claim 40, wherein the antenna support comprises a nonmagnetic material.

43. The tool of claim 40 wherein the means defining the channel further comprises a tube enclosing the antenna support.

44. The tool of claim 39, wherein the means defining the channel is designed to contain high pressure within the channel.

45. The tool of claim 39, wherein the array of permanent magnets is arranged around the means defining the channel.

46. The tool of claim 39, wherein the NMR antenna comprises a solenoidal coil.

47. A well logging tool comprising:

a pumpout module;

means defining a channel that is in fluid connection with the pumpout module;

an array of permanent magnets arranged around the channel to generate a static magnetic field within the channel; and a microwave resonator arranged around the channel to generate an oscillating magnetic field within the channel.

48. The tool of claim 47, wherein the means defining the channel comprises a resonator support in which the microwave resonator is embedded.

49. The tool of claim 48, wherein the resonator support comprises a nonmagnetic material.

50. The tool of claim 48 wherein the means defining the channel further comprises a tube enclosing the resonator support.

51. The tool of claim 47, wherein the means defining the channel is designed to contain high pressure within the channel.

52. The tool of claim 47, wherein the array of permanent magnets is arranged around the means defining the channe.

53. The tool of claim 47, wherein the microwave resonator comprises a cylindrical microwave cavity.

* * * * *